United States Patent [19]

Caughey et al.

[11] Patent Number: 5,276,059
[45] Date of Patent: Jan. 4, 1994

[54] INHIBITION OF DISEASES ASSOCIATED WITH AMYLOID FORMATION

[75] Inventors: Byron Caughey; Richard Race, both of Hamilton, Mont.

[73] Assignee: The United States of America as represented by the Department of Health and Human Services, Bethesda, Md.

[21] Appl. No.: 912,097

[22] Filed: Jul. 10, 1992

[51] Int. Cl.$^5$ .......................................... A61K 31/135
[52] U.S. Cl. ..................................................... 514/647
[58] Field of Search ........................................ 514/647

[56] References Cited

U.S. PATENT DOCUMENTS

| | | | |
|---|---|---|---|
| 4,806,627 | 2/1989 | Wisniewski et al. | 530/387 |
| 4,816,563 | 3/1989 | Wilson et al. | 530/344 |
| 4,878,891 | 11/1989 | Judy et al. | 604/5 |
| 4,892,814 | 1/1990 | Harrington et al. | 435/5 |

FOREIGN PATENT DOCUMENTS 1529119 12/1989 U.S.S.R.

OTHER PUBLICATIONS

Chem. Abst. 82-80589e (1975).
Scand. J. Immunol. (1990) 31(2): 167-173 (Abstract).
Kawahara et al., Am. J. Pathol. (1989), 134(6): 1305-1314 (Abstract).
Gabizon, et al.; Proc. Natl. Acad. Sci. USA; vol. 85; pp. 6617-6621, Sep. 1988; Biochemistry; "Immunoaffinity Purification and Neutralization of Scrapie Prion Infectivity".
Barry et al.; The Journal of Immunology; vol. 140; pp. 1188-1193; No. 4, Feb. 15, 1988; "Characterization of Prion Proteins with Monospecific Antisera to Syntheis Peptides".
Rosenberg, et al.; The American Neurological Association; 1989; "Dominantly Inherited Dementia and Parkinsonism, with Non-Alzheimer Amyloid Plaques: A New Neurogenetic Disorder".
Pocchiari, et al.; Virol. (1987) 68, 219-223; "Ampoteri-cin B Delays the Incubation Period of Scrapie in Intracerebrally Inoculated Hamsters".
Taraboulos, et al.; Proc. Natl. Acad. Sci. USA; vol. 87, pp. 8262-8266, Nov. 1990; Biochemistry; "Acquisition of Protease Resistance by Prion Proteins in Scrapie-infected Cells does not Require Asparagine-linked Glycosylation".
Oesch, et al.; Biochemistry 1990, 29, 5848-5855; "Identification of Cellular Proteins Binding to the Scrapie Prior Protein".
Butler, et al.; Journal of Virology, May 1988, pp. 1558-1564; "Scrapie-infected Murine Neuroblastoma Cells Produce Protease-Resistant Prion Proteins".
Ladogana, et al.; Journal of General Virology (1992); 73, 661-665; "Sulphate Polyanions Prolong the Incubation Period of Scrapie-Infected Hamsters".
Arnold, et al.; Journal of Bacteriology, Dec. 1988, p. 5765, vol. 170, No. 12; "Inhibition of Cell-Cell Interactions in Myxococcus Xanthus by Congo Red".

(List continued on next page.)

Primary Examiner—S. J. Friedman
Attorney, Agent, or Firm—Knobbe, Martens, Olson & Bear

[57] ABSTRACT

The invention provides a method of treating a mammal having a condition associated with formation of amyloidogenic protein without deposition of amyloid plaques. This treatment includes administering to the mammal a pharmacologically effective amount of Congo Red or a pharmaceutically acceptable salt or derivative thereof to interfere with amyloidogenic protein formation or to destabilize amyloidogenic protein structures already formed in said mammal. The invention also provides a method of treating a mammal having a condition associated with deposition of amyloidogenic protein in plaques, and a method of inhibiting the transformation of PrP-sen to PrP-res in a tissue culture sample containing PrP-sen.

34 Claims, 3 Drawing Sheets

OTHER PUBLICATIONS

Gorevic, et al.; Blood Purification 6:132-144 (1988); "Dialysis Amyloidosis: Beta-2 Microglobulin in the Context of Other Amyloidogenic Proteins".

Krasusky; Problems of Tuberculosis; "The Surgical Treatment of Tuberculosis Located In Bones and Joints According to a Report from Krakovskaya Hospital, Moscow Region"; Dept. of Surgery, Krakovskaya Hospital; #4, 1938. (with English translation).

Alan S. Cohen; Bulletin on the Rheumatic Diseases; vol. 40, No. 2; "Amyloidosis", (1986).

Kagan, et al.; Problemy Tuberkuleza 9: 72-72 (1974) "Inhibition of amyloidogenesis by Congo Red during experimental amyloidosis" (with partial translation).

The New England Journal of Medicine; Aug. 23, 1990; "New Frontiers in the Study of Amyloidosis".

Caughey et al.; Journal of Neurochemistry; Rapid Communication; pp. 001-004; "Potent Inhibition of Scrapie-Associated PrP Accumulation by Congo Red" (1992).

Prusiner, et al.; "Novel Mechanisms of Degeneration of The Central Nervous System—Prion Structure and Biology"; pp. 239-262 (1988).

Tareyev, et al.; Medical Case No. 5,1935; "Regarding the Functional Diagnosis of the Reticuloendothelial System during Malaria"; Clinical Dept. of Tropical Diseases Institute of Moscow; pp. 1-6 (with English translation).

INHIBITION OF DISEASES ASSOCIATED WITH AMYLOID FORMATION

BACKGROUND OF THE INVENTION

Amyloid plaque formation is found in a number of diseases including Alzheimer's Disease (AD), scrapie, bovine spongiform encephalopathy, Gerstmann-Straussler Syndrome and related transmissible spongiform encephalopathies (T'SEs). These amyloid plaques comprise protein molecules bound together in a fibrinous matrix. Other disorders, such as Creutzfeldt-Jakob's disease, are characterized by the accumulation of amyloidogenic protein without deposition of amyloid plaques. Together these groups of conditions are referred to herein as "Amyloidogenic Diseases."

Amyloidogenic diseases include a heterogeneous group of hereditary and nonhereditary disorders related by their production of amyloid-forming proteins. These disorders are often accompanied by extracellular deposition of amyloid plaques in one or more tissues. An amyloid plaque is identified by its amorphous, eosinophilic, homogeneous appearance. A unique green birefringence after Congo Red staining, fibriflar ultrastructure, and cross beta X-ray diffraction pattern are also features of amyloid plaques.

The presence of amyloid plaques in various tissue samples can indicate a vast array of diseases. Alzheimer's disease is now identified by the presence of cerebral amyloid plaques derived from beta protein. Adult Type II diabetes can be identified by the presence of the amyloidogenic protein IAPP in amyloid plaques from pancreatic islets.

Some methods of affecting amyloidogenic protein accumulation have been developed. However, no general therapy directed towards many Amyloidogenic Diseases has yet been developed.

In one study of factors affecting amyloid protein accumulation, the drugs melphalan and prednisone were compared with the known protein inhibitor colchicine. Patients treated with colchicine had a median survival of 18 months compared to a control group who survived, on average, only six months. Patients treated with melphalan and prednisone survived 25 months. This study showed no significant difference in survival between subjects in any group, although the trend favored melphalan and prednisone.

Other modes of therapy have included the use of dimethyl sulfoxide and treatment of secondary amyloid with affiylating agents. An experimental fish oil diet in mice has also been studied.

In selected patients with systemic amyloidosis and azotemia, renal transplantation has exhibited effectiveness. Normal renal function may be present for a period of time after transplantation, although amyloid plaques may subsequently develop. Three year graft survival in patients receiving primary cadaveric kidney grafts has been reported, but overall survival of patients with amyloidosis has been worse than patients undergoing transplantation for glomerulonephritis. Notwithstanding the partial success of transplantation, a non-surgical intervention would be more desireable.

In scrapie, Creutzfeldt-Jakob's disease, bovine spongiform encephalopathy, and related transmissible spongiform encephalopathies, an abnormal protease-resistant isoform of the endogenous prion protein (PrP) accumulates in the CNS and other tissues. Unlike the normal, protease-sensitive PrP (PrP-sen), the protease-resistant PrP (PrP-res) is insoluble in many detergents and can aggregate into amyloid-like plaques with high 0-sheet content. Although the etiology of these T'SEs is not clear, evidence exists that PrP plays an important role in the pathogenesis of these diseases.

Some investigators have proposed that PrP-res is a component of the infectious agent or is itself the agent, but this issue remains highly controversial. Studies of the mechanism of PrP-res formation, the relationships of PrP-res to pathogenesis and infectivity, and potential therapies for the T'SEs would be aided greatly by the availability of a compound that selectively inhibits the accumulation of PrP-res.

The structure of Congo Red dye is shown below:

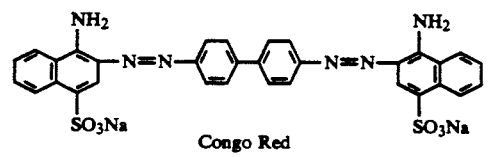

Congo Red is known to bind amyloid plaques, including those comprised of PrP-res protein. See Prusiner et al., Cell, 35:349-358 (1.983). Congo Red has also been reported to inhibit experimental casein-induced amyloid deposition in mice (Kagan et al., Problemy Tuberkuleza, 9:72-74 (1974). However, Applicants are aware of no previous uses of Congo Red in the treatment of Amyloidogenic Diseases.

The disparate presence of amyloid formations throughout the body appears to validate the notion that amyloidosis is a widespread metabolic disease. Thus, a treatment common to all such diseases would provide tremendous benefits.

SUMMARY OF THE INVENTION

Figure 1:
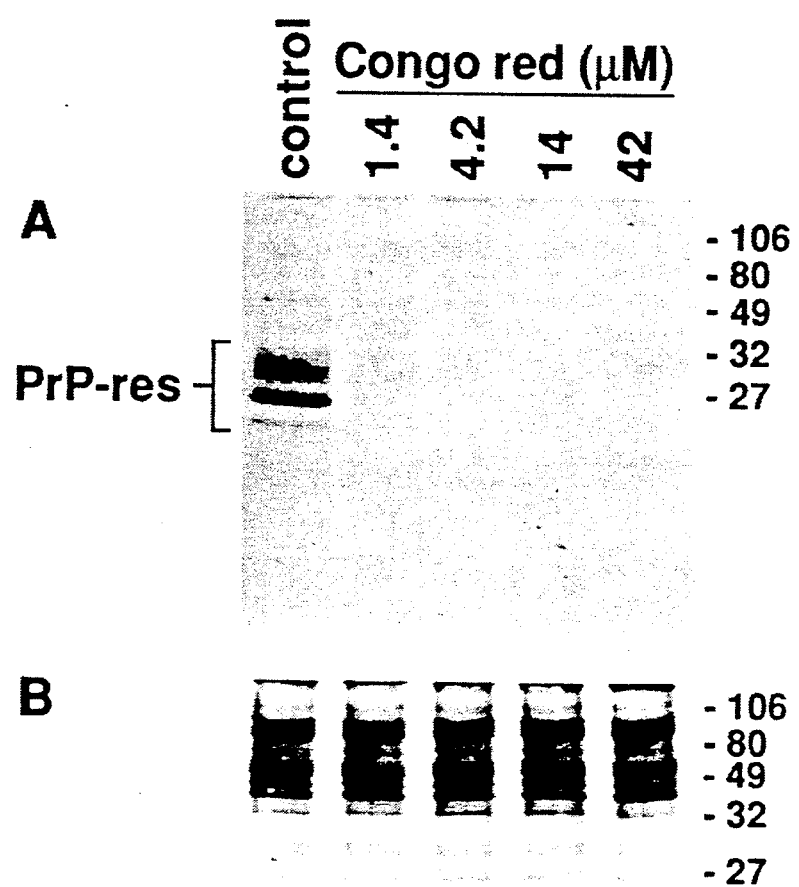
FIG. 1 is an autoradiogram of a gel showing the effect of Congo Red on the metabolic labeling of PrP-res (A) versus total lysate proteins (B).

The present invention relates to a variety of methods of treatment, prevention and/or inhibition of Amyloidogenic Diseases in mammals. In these methods Congo Red or a pharmaceutically acceptable salt or derivative thereof is administered to a mammal having an Amyloidogenic Disease. Thus, in one aspect of the present invention, there is provided a method of treating a mammal having a condition associated with formation of amyloidogenic protein without deposition of amyloid plaques. In this aspect of the invention, a mammal requiring this treatment is identified, and a pharmacologically effective amount of Congo Red or a pharmaceutically acceptable salt or derivative thereof is administered to the mammal in an amount sufficient to interfere with amyloidogenic protein formation or to destabilize amyloidogenic protein structures already formed in the mammal. This aspect of the present invention includes the treatment of Creutzfeldt-Jakob Disease and other Amyloidogenic Diseases associated with formation of PrP-res. The Congo Red can be administered in a pharmacological composition with pharmaceutically acceptable carriers, fillers or excipients. Such a composition can also include a lipophilic solvent or carrier, such as DMZ, an organic solvent, phosphatidyl choline or cholesterol. Administration can be oral or parenteral, with preferred administration routes including transdermal administration, subcutaneous injection, intravenous injection, intraperitoneal injection, intramuscular injection, intrasternal injection, intrathecal injection and infusion techniques.

In another aspect of the present invention, there is provided a method of treating a mammal having a condition associated with deposition of amyloidogenic protein in plaques. This method includes identifying a mammal having such a condition and administering to the mammal a pharmacologically effective amount of Congo Red or a pharmaceutically acceptable salt or derivative thereof in an amount sufficient to interfere with amyloidogenic protein formation or to destabilize amyloidogenic protein structures already formed in the mammal. In a manner similar to the foregoing aspect of the present invention, the Congo Red can be administered in a pharmacological composition with pharmaceutically acceptable carriers, fillers or excipients. Such a composition can also include a lipophilic solvent or carrier, such as DMZ, an organic solvent, phosphatidyl choline or cholesterol. Administration can be oral or parenteral, with preferred administration routes including transdermal administration, subcutaneous injection, intravenous injection, intraperitoneal injection, intramuscular injection, intrasternal injection, intrathecal injection and infusion techniques. This aspect of the invention includes treatment of a large number of such Amyloidogenic Diseases, including the following: scrapie, transmissible spongioform encephalopathies (TSE's), Alzheimer's Disease (AD), hereditary cerebral hemorrhage with amyloidosis Icelandic-type (HCHWA-I), hereditary cerebral hemorrhage with amyloidosis Dutch-type (HCHWA-D), Familial Mediterranean Fever, Familial amyloid nephropathy with urticaria and deafness (Muckle-Wells syndrome), myeloma or macroglobulinernia-associated idopathy associated with amyloid, Familial amyloid polyneuropathy (Portuguese), Familial amyloid cardiomyopathy (Danish), Systemic senile amyloidosis, Familial amyloid polyneuropathy (Iowa), Familial amyloidosis (Finnish), Gerstmann-Staussler-Scheinker syndrome, Medullary carcinoma of thyroid, Isolated atrial amyloid, Islets of Langerhans, Diabetes type II, and Insulinoma. Many of these conditions are associated with deposition of PrP-res. In a preferred form of the invention, the method is useful for treating, preventing and/or inhibiting conditions associating with plaques occurring in a tissue of the central nervous system of said mammal. In another form, the method useful against a disease of the internal organs related to amyloid plaque formation, including plaques in the heart, liver, spleen, kidney, pancreas, brain, lungs and muscles. Thus, in this form, the method includes treatment of Adult type II diabetes where the plaques occur in the pancreas. In still other forms of this aspect of the invention the condition is associated with deposition of a variant form of cystatin-C, such as HCHWA-I, or a form of amyloid precursor protein (APP), such as AD or HCHWA-D.

In yet another aspect of the present invention, there is provided a method of inhibiting the transformation of PrP-sen to PrP-res in a tissue culture sample containing PrP-sen. In this aspect, Congo Red or a salt or derivative thereof in an amount effective to interfere with PrP-res formation is applied to the sample. In a preferred form of this aspect, the sample can include COST cells.

The present invention includes still another aspect in which a method of treating a mammal, such as a human, having a condition associated with overproduction of PrP-res is provided. In this aspect, such a mammal is identified and treated with Congo Red in a manner, such as that described above in the foregoing aspects of the invention.

In still a further aspect of the present invention, there is provided a method of treating a mammal having a chronic infection associated with Acquired Amyloid protein. These infections include tuberculosis, osteomyelitis, rheumatoid arthritis, granulomatous ileitis, and Mediterranean fever. The method includes identifying such a mammal and administering Congo Red, in a manner such as that described above for other aspects of the invention.

In yet one more aspect of the present invention, a method of treating a mammal having multiple myeloma associated with Idiopathic Amyloid protein is provided. This method includes identifying a mammal having multiple myeloma associated with Idiopathic Amyloid protein, such as one derived from the variable region portion of an immunoglobulin protein. Congo Red or a suitable salt or derivative is then administered to the mammal in an amount sufficient to interfere with amyloidogenic protein formation or to destabilize amyloidogenic protein structures already formed in said mammal.

DETAILED DESCRIPTION

The Applicants' have discovered that Congo Red not only binds amyloid plaques, but can also inhibit the accumulation of amyloidogenic protein. In this regard, Applicants have further discovered that administration of Congo Red to a mammal in vivo can provide effective treatment, prevention and/or inhibition of many, if not all Amyloidogenic Diseases. In particular, the invention can be used for both Amyloidogenic Diseases associated with deposition of amyloid plaques and Amyloidogenic Diseases, such as Creutzfeldt-Jakob Disease, in which formation of amyloidogenic protein occurs without deposition of amyloid plaques. The ultimate treatment of the present invention is aimed at decreasing amyloidogenic protein accumulation and deposition by inhibiting its formation or decreasing its metabolic stability.

Amyloid plaques comprise amyloidogenic protein molecules bound in a fibriflous matrix and deposited on the cell surface. The present invention describes a method of inhibiting the accumulation of these plaque-forming proteins in vitro and in vivo by Congo Red.

It is now possible to clinically classify the various amyloid proteins based on the nature of their biochemistry. Applicants believe that inhibition of the accumulation of these types of amyloidogenic proteins by Congo Red would inhibit amyloid fibril formation possibly leading to cessation or stabilization of the disease state. Table I lists a variety of Amyloidogenic Diseases along with their associated amyloidogenic proteins.

Applicants believe that Congo Red has the ability to reduce the amount of amyloidogenic protein production associated with many Amyloidogenic Diseases, inlcuding those listed in Table 1. Thus, the administration of Congo Red to a mammal having one of these conditions is believed to be beneficial in the inhibition, prevention and treatment of these diseases.

TABLE 1

The 1990 guidelines for nomenclature and classification of amyloid and amyloidosis

| Amyloid Protein[a] | Protein Precursor | Clinical |
|---|---|---|
| AA[b] | apoSAA | Reactive (secondary) |
|  |  | Familial Mediterranean Fever |
|  |  | Familial amyloid nephropathy with urticaria and deafness (Muckle-Wells syndrome) |
| AL | kappa, lambda (e.g., k III) | Idiopathic (primary), myeloma or macroglobulinernia-associated |
| AH | IgG 1 ($\gamma$1) |  |
| ATTR | Transthyretin | Familial amyloid polyneuropathy (Portuguese) |
|  |  | Familial amyloid cardiomyopathy (Danish) |
|  |  | Systemic senile amyloidosis |
| AApoAI | apoAI | Familial amyloid polyneuropathy (Iowa) |
| AGel | Gelsolin | Familial amyloidosis (Finnish) |
| ACys | Cystatin C | Hereditary cerebral hemorrhage with amyloidosis (Icelandic) |
| AB | B protein precursor (e.g., BPP 695) | Alzheimer's disease |
|  |  | Down's syndrome |
|  |  | Hereditary cerebral hemorrhage amyloidosis (Dutch) |
| AB$_2$M | B2-microglobulin | Associated with chronic dialysis |
| AScr | Scrapie protein, precursor 33–35f cellular form | Creutzfeldt-Jakob disease, etc. Gerstmann-Staussler-Scheinker syndrome |
| ACal | (Pro)calcitronin | Medullary carcinoma of thyroid |
| AANF | Atrial natriuretic factor | Isolated atrial amyloid |
| AIAPP | Islet amyloid polypeptide | Islets of Langerhans Diabetes type II, Insulinoma |

[a]Non-fibrillar proteins, e.g., protein AP (amyloid P-component) excluded
[b]Abbreviations not explained in table: AA = amyloid A protein; SAA = serum amyloid A protein; apo = apolipoprotein; L = immunoglobulin light chain; H = immunoglobulin heavy chain Amyloid plaques associated with chronic infections such as tuberculosis, osteomyelitis, rheumatoid arthritis, granulomatous ileitis, and many types of Mediterranean fever are composed of protein AA, an approximately 8,500 Dalton, 76 amino acid molecule, heterogenous at the amino terminus. AA proteins have been isolated from a variety of species. The amino acid sequence of the AA protein in various human diseases is similar, contrasting the idiopathic amyloids that exhibit individual variability. The AA protein's putative precursor is serum amyloid A (SAA), a 12.5 kd (104 amino acid) polymorphic protein with multiple isoforms (Table 1). The human SAA family consists of six similar but distinct proteins.

One in vivo model of amyloidosis in hamsters produces amyloidogenic plaques in the hamsters believed to be caused by AA protein. The following experiment describes one method of inhibiting amyloidosis in hamsters in this model using Congo Red.

In Vivo Experiment Using Syrian Hamsters

Female Syrian hamsters (available from Charles River Labs) normally develop amyloidosis of the liver, spleen and kidney one year after birth, resulting in a much shorter life expectancy for females than for males (Coe & Ross, J Clinical Investigation 76:66–74 (1985)). The amyloidosis can be accelerated markedly by the administration of diethylstilbestrol (DES) so that it occurs within 2-3 months of initiating treatment.

To determine the effects of Congo Red on amyloidosis in this model, four groups of hamsters are compared. The first group (10 hamsters) are given DES pellets at 3 months of age followed by a continuous treatment of 2 intraperitoneal injections of 0.5 mg Congo Red per week. The second group (10 hamsters) receive only the DES pellets. The third group (10 hamsters) receive only Congo Red treatments at intervals coinciding with group 1. The fourth group (10 hamsters) receives injections of sterile water at intervals coinciding with group 1 injections.

All animals are analyzed for amyloid deposits in the liver, spleen and kidney by a tissue squash method (Coe and Ross, J. Exp. Med 171:1257–67 (1990)) after 4 months. The hamsters injected with DES and Congo Red show a reduction in the amount of amyloid deposits compared with group 2 (DES alone). This result shows inhibition of amyloid plaque formation by Congo Red.

AL Protein

Another type of amyloid plaque comprises the AL protein, normally detected in patients with multiple myeloma. AL protein consists of a variable region portion of either the kappa or lambda immunoglobulin light chains. In some cases the entire kappa or lambda protein molecule is detected. While kappa chain amyloids are prevalent in multiple myeloma and monoclonal gammopathies, the incidence of lambda chain amyloids predominates by a 2:1 ration. The AL protein amino acid sequence is identical from afl the organs of any one patient. Virtually all kappa and lambda chain proteins known to date are amyloidogenic although some seem to be more susceptible to plaque formation than others.

Amyloid Beta Protein

It has been known for years that brain tissue from Alzheimer's disease (AD) patients contained amyloid plaques which were stainable with Congo Red. Amyloid fibrils from the cerebral blood vessels of AD and from Down's syndrome patients were isolated and found to be caused by the amyloid beta protein (AIBP). This protein has now been accepted as a probable factor in the pathogenesis of AD. Alpha-1 antichymotrypsin (a serine proteinase inhibitor) was also shown to be intimately associated with beta protein in AD. An enormous number of studies have been done confirming that APB derives from an amyloid precursor protein (APP or ABPP).

In the Dutch type cerebral amyloid with hemorrhage syndrome, the amyloid plaque also comprises a beta protein but with a variant amino acid (Gln 22). The original Icelandic form of this disease comprises an amyloid protein of cystatin C with one variant amino acid (Gln 68). Applicant believes that Congo Red treatment of these diseases may cause a reduction in the level of amyloid protein accumulation.

TSE's

The transmissible dementias or spongioform encephalopathies such as Creutzfeldt-Jakob disease, Gerstmann-Straussler syndrome, kuru and a variety of animal diseases such as scrapie, are all characterized by abnormal accumulations of PrP-res which often results in amyloid plaques. Thus, inhibition of PrP-res accumulation by Congo Red can be used in vivo as a treatment for these diseases.

Amyloid Formation

Extensive studies have been carried out to assess common factors or substances related to all the amyloid-forming proteins, so far without success. However, the most prominent mechanism proposed for amyloid formation involves the P component of amyloid (AP) and its serum counterpart (SAP). Electron microscopy reveals that AP is a 230 kD protein composed of a pair of pentagonally shaped subunits. AP may serve as a scaffold for amyloid fibril formation.

When isolated, AP is distinct from an amyloid plaque, does not bind Congo Red, and is without any fibrillar ultrastructure or cross beta pattern. However, AP has been found in virtually an known forms of amyloid.

Glycosaminoglycans (GAGS) have also been prominently associated with amyloid. Multiple studies have attempted to relate specific GAGs to amyloid deposits. Since most amyloids are associated with highly sulfated GAGS, it has been postulated that these very negatively charged molecules affect the protein product or precursor processing.

Traditional studies have regarded amyloid formation as a two-phase process. In the first phase, the production of amyloidogenic precursor proteins is initiated. In the second phase, amyloid fibril deposition or processing occurs. Amyloid enhancing factor (AEF) is known to, for example, shorten either the lag between phases or induction time. This elusive substance has been found in both animal and human amyloid plaques, but is not yet precisely characterized.

Applicants believe that Congo Red can inhibit amyloidogenic protein production at the first phase of the process. Thus, Applicants believe that Congo Red provides a general method of treatment, prevention and inhibition that is common to all Amyloidogenic Diseases.

Identification of Amyloidosis

Amyloidosis is normally suspected in individuals with unexplained renal disease, especially those with nephrotic syndrome. Also suspect are individuals with hepatosplenomegaly in association with certain chronic inflammatory disorders such as rheumatic disease. Congo Red treatment may provide an effective treatment for these disorders. Amyloidosis could be considered in patients with a wide range of diseases, for example, carpal tunnel syndrome, macroglossia, neuromuscular disease, congestive heart failure or malabsorption. Especially suspect are individuals with plasma cell neoplasms or a homogeneous immunoglobulin in the serum or urine.

Patients with AL amyloidosis frequently have Bence Jones proteins alone or in association with a serum monoclonal protein. In patients suspected of having AL amyloidosis, an examination of the bone marrow can document the underlying plasma cell dyscrasia or possible myeloma. This type of examination can also be used to search for amyloid infiltrates, which can often be found in bone marrow.

Reactive (AA) (secondary) amyloid is classically associated with chronic inflammatory and infectious diseases. In recent years, it has become apparent that amyloid may complicate Crohn's disease with an incidence of at least 1% and that it is a serious complication of chronic drug abuse. Patients with cystic fibrosis have also been found to have amyloidogenic plaques.

Candidates for hereditary amyloidosis include those with family histories of neuropathy with early sensorimotor dissociation especially when it is associated with carpal tunnel syndrome, vitreous opacities, or renal or cardiovascular disease.

Specific clinical manifestations of amyloidosis vary enormously, depending greatly on the involved organ and the extent of the deposits. The following comments refer largely to generalized (systemic) amyloid, i.e., reactive (secondary), idiopathic (primary) or heterofamilial, respectively.

Renal involvement is common in almost all forms of systemic amyloid, ranging from mild urinary red blood cell loss or mild proteinuria to extensive nephrosis. A renal lesion is usually irreversible possibly leading to progressive azotemia.

Hepatic enlargement from amyloid deposition is common, while signs of portal hypertension from hepatic amyloid plaques are uncommon. Hepatic cholestasis with severe liver involvement can also occur due to amyloidosis, although liver function abnormalities, especially elevated serum alkaline phosphatase, are usually minimal, occurring late in the disease. Liver scans are known to produce variable and nonspecific results.

Gastrointestinal symptoms in amyloidosis are very common and result from direct involvement of the gastrointestinal tract from infiltration of the autonomic nervous system with amyloid. The symptoms include those of obstruction, ulceration, hemorrhage, malabsorption, protein loss and diarrhea.

Cardiac manifestations of amyloidosis consist primarily of congestive heart failure and cardiomegaly. Intractable heart failure may be the first manifestation and is the major cause of death in patients with generalized amyloidosis. Although cardiac manifestations normally indicate predominantly diffuse myocardial amyloid plaques, the endocardium, valves, and pericardium may be involved.

Clinically significant amyloid heart disease is common in the AL form and rare in AA form of the amyloid plaque. In an echocardiographic study of 28 patients with FAP, it was shown that heart disease develops slowly but progressively and that left ventricular diastolic abnormalities precede the development of clinically overt heart disease. Isolated cardiac amyloidosis itself has been reported as a cause of sudden death. Finally, senile cardiac amyloid has been shown to be a cause of congestive heart failure.

Amyloid is identifiable in the skin in over one-half of patients with primary or secondary disease, whether or not clinically apparent lesions are present. The lesions vary widely from waxy, often translucent, papules or plaques to nodules or tumefactions. Purpuric areas may be present. The lesions are seldom pruritic. Involvement of the skin or mucosa may not be apparent even on close inspection but may be discovered at biopsy. Patients with hereditary amyloid neuropathy have positive skin biopsies for amyloid in most cases.

Amyloidosis is infrequently seen in the synovium of patients with AA (secondary) disease, but it has been found in AL (primary) and in disease associated with chronic hemodialysis (beta-2-microglobulin). In rare instances of AL it can mimic rheumatoid arthritis and has been associated with a fullness in the shoulder called the "shoulder pad syndrome". It has surprisingly a frequent association with osteoarthritis. Amyloidosis can also accumulate in the muscles causing a frank myopathy.

The $\beta 2M$ amyloid of chronic hemodialysis was first found in the lesions of carpal tunnel syndrome, but is now known to cause an extraordinary variety of bone and joint lesions ranging from carpal tunnel syndrome to destructive arthropathy and cystic bone lesions. Kidney transplants have been shown to halt the progression and cause symptomatic relief, but have not as yet been shown to reverse the lesions.

Neurologic manifestations that are especially prominent in the classic hereditary neuropathies include peripheral neuropathies with early sensorimotor dissociation, and autonomic nervous system involvement with constipation, diarrhea, impotence, and postural hypertension. Except for the Finnish variety of hereditary neuropathy, cranial nerves other than those involving pupiuary reflexes are generally spared.

It has been well known for many years that reactive (secondary, AA) amyloidosis is a major complication of rheumatoid arthritis. The early literature reported its incidence in a variety of ways, including renal biopsies, rectal biopsies, Congo Red tests, gingival biopsies, and with a variety of tissue stains, such that its true incidence was not clear.

The earlier literature was also affected by the method in which amyloid was diagnosed in the tissue. Crystal violet metachromasia and other histochemical and fluorescent stains as well as Congo Red were utilized. The current standard for amyloid identification is the demonstration of green birefringence on polarization microscopy after Congo Red staining and has been generally accepted in the literature since 1980. Although Congo Red has been used as a stain to identify many of the above disease states, Applicants have discovered that Congo Red can be used in vivo to inhibit amyloidogenic protein accumulation.

Treatment of Amyloidosis Condition without Plaque Formation

As stated above, a number of Amyloidogenic Diseases in mammals occur without actual completion of the plaque forming phase. In this diseases, the amyloidogenic proteins themselves are involved in the diseases-producing process. Cruezfeldt-Jakob Disease is one example of such a disease.

The Applicants believe that a mammal suffering from amyloid protein production can be effectively treated by administration of a pharmaceutically effective composition of Congo Red. For instance, Congo Red (or its pharmaceutically acceptable salt or derivative) can be given to a mammal in need of such a treatment by oral or parenteral administration. Preferred administration methods include intravenous injection, transdermal administration, intraperitoneal injection, subcutaneous injection, intramuscular injection, intrasternal injection, intrathecal injection or direct infusion techniques.

Use of appropriate Congo Red derivative compounds that retain the ability of Congo Red to interfere with generation and/or deposition of amyloidogenic protein are included within the scope of the present invention.

Preferred dosages in the treatment of Amyloidogenic Diseases in mammals are generally in the range of 1 $\mu g/kg$ to 100 mg/kg. More preferably, the dosage is between 0.01 mg/kg and 10 mg/kg.

The Congo Red can be administered in solution in water. However, in certain preferred embodiments of the present invention, a pharmaceutically acceptable carrier, filler, or excipient. Congo Red can also be administered in a lipophilic solvent or carrier to provide advantageous in vivo effects. Lipophilic solvents and carriers include such compounds as Dimethyl Sulfoxide (DMSO), phosphotidyl choline, or cholesterol.

Example of Treatment for Patient with Amyloidosis

A patient suffering from Cruezfeldt-Jakob's disease is given an intravenous injection comprising a pharmaceutically active concentration of Congo Red in deionized water. Three weeks later, the patient's progression of the disease state is measured. The patient performs at a higher level of functioning than prior to Congo Red injection. This example indicates the potential of Congo Red to inhibit diseases which relate to amyloidogenic protein production without plaque formation.

Treatment of Amyloidogenic Diseases Associated with Plaque Formation

The following examples describe methods of using Congo Red to inhibit plaque formation in amyloidogenic diseases having this type of manifestation. As discussed in more detail above, there are many diseases resulting in amyloid plaque formation including, transmissible spongioform encephalopathies (TSE's), Alzheimer's Disease (AD), hereditary cerebral hemorrhage with amyloidosis Icelandic-type (HCHWA-1) and hereditary cerebral hemorrhage with amyloidosis Dutch-type (HCHWA-D).

Treatment of TSE's

A patient suffering with a transmissible spongioform encephalopathy (TSE) is intravenously injected with a pharmaceutically effective concentration of Congo Red. Prior to treatment, a tissue biopsy finds that the patient has a large number of amyloid plaques comprising PrP-res. The Congo Red solution is injected into the patient in a phosphotidyl choline carrier. The number of amyloid plaques in a secondary tissue biopsy finds a reduction in the number of PrP-res amyloid plaques after Congo Red treatment. Reducing number of amyloid plaques results in a further medical improvement of the patient. This is one method of successfully treating a patient diagnosed with TSE using Congo Red.

Effect of Congo Red on PrP-res Accumulation in Scrapie-Infected Mice

Another example of using Congo Red in the prevention of an Amyloidogenic Disease associated with deposition of PrP-res is provided below. In this example, the Amyloidogenic Disease is scrapie in mice.

Weanling random bred RML Swiss mice were inoculated intraperitoneally with 50 µl 1% brain homogenate from mice clinically ill with scrapie (Chandler strain) containing $10^4$–$10^5$ $LD_{50}$ scrapie agent. One group of eight mice was given twice weekly intraperitoneal injections of 0.5 mg Congo Red (in sterile water) starting within 6 hours of the scrapie inoculation. A control group of eight mice was given intraperitoneal injections of water alone.

After five weeks, the spleens were harvested from all the animals. The pulp cells from individual spleens were sonicated, treated for 1 h with 33 µg/ml DNAase A (37° C.), combined with an equal volume of 20% sarkosyl, and centrifuged at 10,000 rpm in a Beckman TL100.4 rotor for 30 min. The supernatants were then centrifuged at 70,000 rpm for 2 hr. The pellets were resuspended in 10 mM Tris-HCL, pH 7.5, sonicated, treated with 10 jig/ml proteinase K for 30 min (37° C.) and then repelleted at 70,000 rpm. The pellets were then analyzed for PrP-res by immunoblot using anti-PrP antiserum using standard procedures. The average immunoblot signal intensity of PrP-res from spleens of Congo Red injected animals was 87% less than the average control value. This result suggests that Congo Red treatment in vivo can substantially reduce the accumulation of PrP-res.

Another example of treatment of an Amyloidogenic disease is provided below. In this example, the beneficial effects of Congo Red are measured by the increase in life span in hamsters infected with scrapie agent.

Effect of Congo Red on the Incubation Time of Scrapie in Hamsters

Weanling Syrian hamsters (available from Charles River Laboratory) are inoculated intraperitoneally with 0.5%, 1.0%, and 2.5% dilutions of brain tissue from hamsters in the clinical stages of scrapie (263K strain). 50 hamsters are treated with intraperitoneal injections of water alone (control). 50 hamsters are treated with 50 µl of a 1% Congo Red solution in sterile water beginning several hours before the scrapie inoculation and continuing twice weekly for the life of the animal. The animals injected with Congo Red have a much longer life span due to reduction in their disease state. These results indicate that Congo Red can inhibit scrapie (a PrP related disease) in vivo.

In Vitro Experiments of Mouse Neuroblastoma Cells

In the following in vitro experiments, Applicants demonstrate that accumulation of PrP-res in mammalian cells can be inhibited by Congo Red. Scrapie-infected mouse neuroblastoma cells were used as a model to study prion protein (PrP) accumulation.

Identically seeded, nearly confluent 25-cm² flasks of scrapie-infected mouse neuroblastoma cells (Race, et al. 1988) were rinsed twice with phosphate-buffered balanced salt solution and preincubated in 2 mi of methionine-free and cysteine-free minimal essential medium with 1% dialyzed fetal bovine serum at 37° C. After 30 min. an aqueous concentrate of Congo Red (Sigma) was added to the medium to give the designated final concentrations. Immediately thereafter, 380 lici of Tran$^{35}$S-label (ICN) was added to each flask for a 2-h pulse labeling. Following the radiolabled nucleotides was 10 ml of chase medium (complete minimal essential medium with 10% fetal bovine serum) containing the designated Congo Red concentration, and incubation continued for 16 h to allow the labeling of PrP-res.

Cell lysates were prepared by standard protocols and, following the removal of aliquots for the total labeled protein analysis, radiolabeled PrP-res concentrations were measured using a previously described procedure (Caughey and Raymond, 1991). In brief, the lysates were treated with proteinase K and ultracentrifuged to isolate PrP-res. The PrP-res was then solubilized, immunoprecipitated with a rabbit antiserum to PrP peptide 89–103 (Caughey et al. *J. Virol* 65:6597–6603 (1991)), and analyzed by sodium dodecyl sulfate (SDS)-polyacrylamide gel electrophoresis (PAGE) and fluorography. A 20% acrylamide Pharmacia LYB PHAST-SYSTEMO gel was used for the SDS-PAGE.

Release of Labeled PrP-sen from Intact Cells

Nearly confluent flasks of cells were preincubated with fresh minimal essential medium containing 10% fetal bovine serum for 20 h. The ceils were then rinsed, preincubated in methionine- and cysteine-free medium, labeled with 100 µCi of Tran$^{35}$S-label for 90 min, and chased for 30 min according to the general procedure described above. After rinsing with phosphate-buffered balanced salts solution, the cells were incubated for 30 min at 37° C. with phosphatidyl-inositol-specific phospholipase C (PIPLC) from *Bacillus thuringiensis* (Low, et al. (1988) *C. J Immunol Methods* 113: 101–111) at an activity of 1.6 limol/min. The PIPLC media was centrifuged at 1,000 g for 2 min, and the supernatants adjusted to a final concentration of 0.5% sodium deoxycholate, 0.1% SDS, 1% Nonidet P-40, 0.15 M NaCl, 1 mM EDTA, 01.% gelatin, 50 mM Tris-HCI (pH 8.0). 5 µl of antiserum R34 was added to precipitate the PrP-res. The remainder of the immunoprecipitation and analysis by SDS-PAGE-fluorography (12.5 % acrylamide gel) was performed as described previously (Caughey, et al., 1991a).

Immunoblotting

PrP-res separated on a 20 % acrylamide gel was electrophoreticauy transferred onto a polyvinyl difluoride membrane (MiUipore) using the Pharmacia LKB PHASTSYSTF-MO The Membrane was blocked with 5 % nonfat dried milk in 1 0 mM Tris-HCI (pH 8.0), 150 mM NaCl, and 0.05% Tween-20 (TBST). The filter was incubated for 2 h at ambient temperature with anti-PrP serum diluted 1:1000 in TBST. After washing in TBST, the filter was strained with horseradish peroxidase-conjugated goat anti-rabbit immunoglobulin and the ECL luminescence detection kit (Amerisham). Estimates of the relative amounts of PrP-res detected in the immunoblot lanes were obtained by comparing the film exposure times giving densitometrically equivalent band intensities.

In vitro Results

The effect of Congo Red on the accumulation of newly synthesized PrP-sen in scrapie-infected neuroblastoma cultures was tested by metabolically labeling PrP-res in the presence of Congo Red.

Concentrations of Congo Red greater than 1.4 µM nearly eliminated detectable labeling of PrP-res (FIG.

1A). FIG. 1 describes the effect of Congo Red on the metabolic labeling of PrP-res (Lanes A) versus total lysate proteins (Lanes B). PrP-res was $^{35}$S-labeled in scrapie infected neuroblastoma cells in the presence or absence (control) of the designated concentrations of Congo Red. The total lysate proteins were methanol-precipitated from detergent lysates after nuclei and debris removal by low-speed centrifugation. Equal flask equivalents were loaded onto each lane in both panels. The positions of molecular mass markers are designated in kDa on the right side of FIG. 1. The inhibitory effect of 1.4 µM Congo Red on the labeling of PrP-res as shown here was observed in three similar duplicative experiments.

Because the two generally recognized hallmarks of PrP-res are its protease resistance and its aggregated state, a protocol was used employing both proteinase K treatment and ultracentrifugation to discriminate PrP-res from normal PrP. In addition, to test for the possibility that Congo Red decreased the proteinase K resistance of PrP-res without affecting its aggregation state, or vice versa, the experiment was repeated using only proteinase K treatment (followed by methanol precipitation) or ultracentrifugation of the cell lysates before the solubilization and immunoprecipitation of PrP-res. In each case, Congo Red-dependent reductions in PrP-res labeling were observed, indicating that Congo Red inhibited the labeling of PrP-res as defined by either aggregation or proteinase K resistance. The inhibitory effect of Congo Red appeared to be selective for PrP-res since the highest concentrations of Congo Red tested (42 µM) did not change the overall profile of labeled proteins in the cell lysates before proteinase K treatment (FIG. 1B). Furthermore, there were no effects of these Congo Red treatments on cellular morphology.

Since phospholipase-sensitive, cell surface (PrP-sen) is the precursor of PrP-res (Caughey and Raymond, *J. Biol. Chem.* 266:18217-18223 (1991)), it is possible that the newly discovered Congo Red inhibition of PrP-res labeling could be indirectly due to PrP-sen biosynthesis, turnover, or transport to the cell surface. However, 1.4 µM Congo Red had no influence on the [$^{35}$S]methionine labeling and rate of degradation of PrP-sen (FIG. 2) or the release of labeled PrP-sen from the cell surface by PIPLC (FIG. 3).

Figure 2:
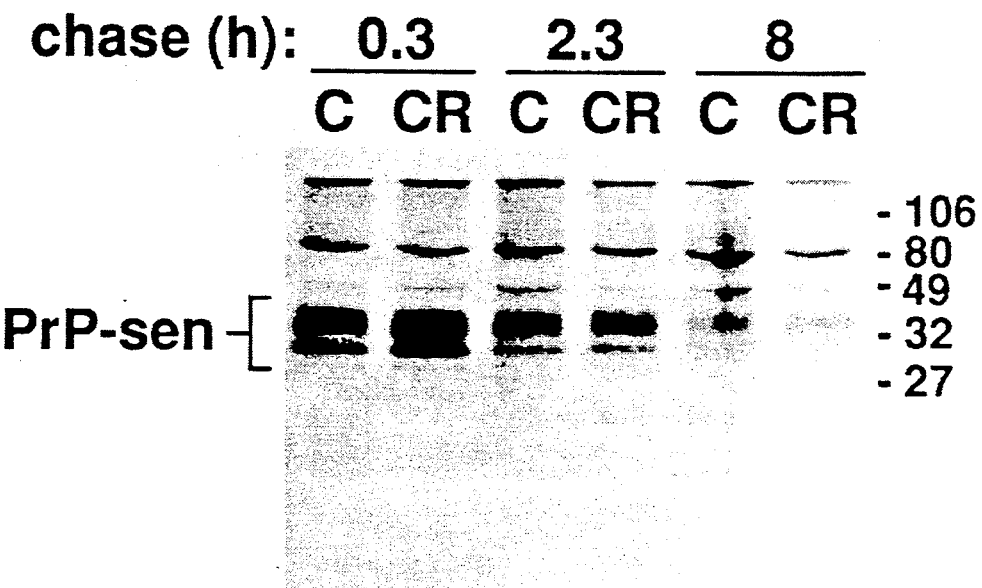
FIG. 2 is an autoradiogram of a gel showing lack of effect of Congo Red (CR) on the metabolic labeling and turnover of PrP-sen.

FIG. 2 shows the results of an experiment to determine the effect of Congo Red (CR) on the metabolic labeling and turnover of PrP-sen. Control (C) flasks of scrapie infected neuroblastoma cells were pulse-labeled with 60 µCi per flask of Tran$^{35}$S-label for 100 min by the general procedure described above and incubated in chase medium for the time indicated before the cells were lysed. Cells were then analyzed for PrP-sen by immunoprecipitation, SDS-PAGE, and fluorography as described previously (Caughey et al., 1991a) except that a 20% acrylamide PHASTSYSTEM© gel was used. The CR-treated flasks were treated identically except that the pulse and chase media contained 1.4 µM CR. Equal flask equivalents were loaded onto each lane. The positions of molecular mass markers are designated in kDa on the right side of FIG. 2. There is no apparent effect of Congo Red on the cellular metabolism of PrP-sen.

Figure 3:
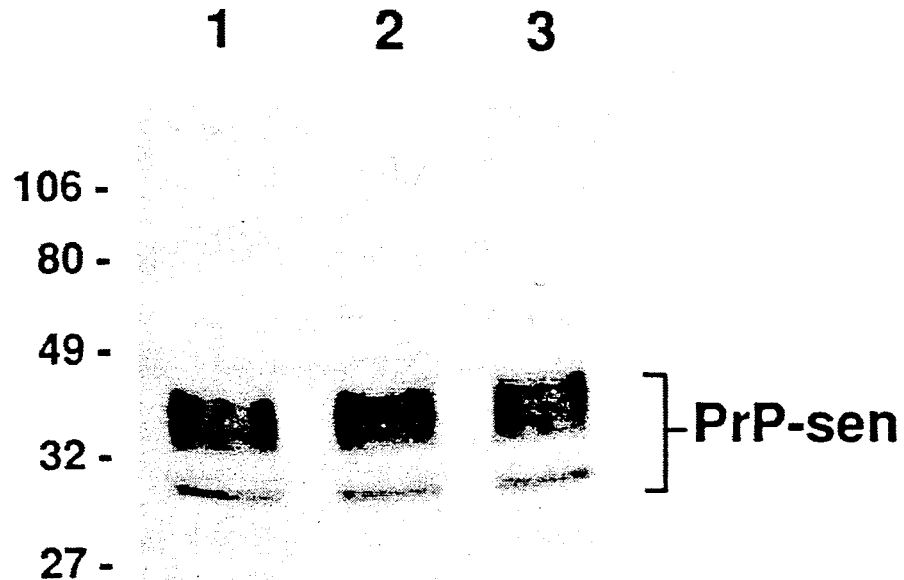
FIG. 3 is an autoradiogram of a gel showing lack of effect of Congo Red on the transport of PrP-sen to the cell surface.

FIG. 3 shows the results of an experiment which confirms the lack of effect that Congo Red has on the transport of PrP-sen to the cell surface. PrP-sen was immunoprecipitated from the media of intact scrapie-infected neuroblastoma cells treated with PIPLC to release pulse $^{35}$S-labeled PrP-sen from the cell surface as described above. The analysis was performed on control cells (no Congo Red; lane 1) and cells treated with 1.4 µM Congo Red starting with the pulse (lane 2) or a 20-h preincubation before the pulse (lane 3). The positions of molecular mass markers are designated in kDa on the left. Equal flask equivalents were loaded onto each lane.

These observations provided evidence that, rather than affecting normal PrP metabolism, Congo Red specifically prevented PrP-res formation or greatly reduced its metabolic t₁.

The longer-term effect of Congo Red on the total PrP-res content of scrapie-infected neuroblastoma cultures was also tested. Inclusion of submicromolar concentrations of Congo Red in the growth medium of 5-day cultures caused profound reductions in the total PrP-res content detected by immunoblot using three distinct antisera raised against peptides corresponding to PrP residues 89-102 (FIG. 4), 142-155, and 218-232. For instance, in FIG. 4, the intensity of PrP-res bands from the cells treated with 0.14 µM Congo Red was $<10\%$ of control intensity.

Figure 4:
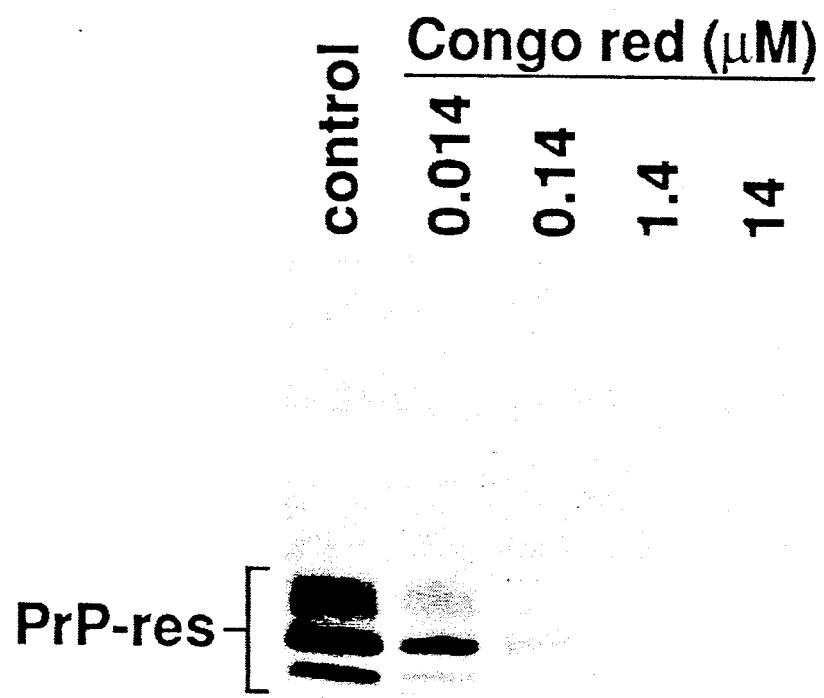
FIG. 4 is a gel showing inhibition of PrP-res accumulation in cells grown in Congo Red.

FIG. 4 shows the inhibition of PrP-res accumulation in cells grown media containing in Congo Red. Scrapie-infected neuroblastoma cells were seeded at a 1:20 dilution of a confluent culture and grown for 5 days to confluence in the presence of the designated concentrations of Congo Red. PrP-res was isolated from proteinase K-treated detergent lysates of the cells by ultracentrifugation. The 230,000-g pellets containing PrP-res were sonicated into 1 ml of 150 Mm NaCl, repelleted, and further analyzed for PrP by immunoblotting as described above. Each lane represents 0.2 25-cm² flask equivalent.

To control for the possibility that residual Congo Red in the lysates artifactually interfered with the immunochemical detection of PrP-res, 14 µM of Congo Red was added to a control cell lysate before proteinase K digestion step. There was no reduction in the PrP-res signal detected by the extraction and immunoblot procedure using anti-PrP peptide 89-102. The treatment of the cells with Congo Red (up to 14 µM) had no significant effect on the growth of the cultures because the total protein content in the lysates of the Congo Red-treated cells was within 85% of the control values in all cases. Again, no changes in cell morphology were observed. Thus, without overt signs of cytotoxicity, Congo Red greatly reduced the amount of PrP-res produced by the infected neuroblastoma cultures.

Mechanism of Action

The mechanism for the inhibition of the accumulation of PrP-res and other amyloidogenic proteins by Congo Red is not known. However, because Congo Red binds to amyloid fibrils of PrP-res it is likely that this direct interaction interferes with a critical event in the formation of amyloidogenic protein or destabilize the structure once it is formed. Destabilization of amyloidogenic protein could make it susceptible to degradation by the endogenous proteases to which it is exposed.

Woody et al., *Biochim. Biopys. Acta* 655:82-88 (1981), have suggested that Congo Red can stack extensively and act as a polyanion. This theory is bolstered by Applicants' discovery that Congo Red can serve to prolong the lifespan of scrapie-infected mammals, since prophylactic administration of certain polyanions has also been shown to prolong the lifespan of animals inoculated with scrapie (Kimberlin and Walker, *Antimicrob. Agents Chemother.* 30:409-413 (1986)).

As stated earlier, use of appropriate derivative compounds that retain the ability of Congo Red to interfere with generation and/or deposition of amyloidogenic protein are included within the scope of the present invention. Thus, appropriate Congo Red derivate compounds for use within the scope of the present invention will include those that do not interfere with the formation of polyanion-like activity in the derivative.

Conclusion

The foregoing detailed description has exemplified Applicants' discoveries with reference to certain particular amyloidogenic proteins and Amyloidogenic Diseases. However, Applicants have discovered a method of treatment, prevention and/or inhibition that is common to many Amyloidogenic Diseases. Other discoveries also form a part of the present invention. Thus, the scope of the present invention can be interpreted with reference to the appended claims.

What is claimed is:

1. A method of treating a mammal having scrapie, comprising:
   administering to said mammal a pharmacologically effective amount of Congo Red or a pharmaceutically acceptable salt or derivative thereof to interfere with amyloidogenic protein formation or to destabilize amyloidogenic protein structures already formed in said mammal.

2. The method of claim 1, wherein said condition is Creutzfeldt-Jakob of prP-res and wherein said amyloidogenic protein comprises PrP-res.

3. The method of claim 1, wherein the administering step comprises administering a pharmacological composition comprising Congo Red or a pharmaceutically acceptable salt or derivative thereof and pharmaceutically acceptable carrier, fillers or excipients.

4. The method of claim 1, wherein the administering step comprises oral administration of Congo Red or a pharmaceutically acceptable salt or derivative thereof into said mammal.

5. The method of claim 1, wherein the administering step comprises parenteral administration of Congo Red or a pharmaceutically acceptable salt or derivative thereof into said mammal.

6. The method of claim 5, wherein the administering step comprises a technique selected from the group consisting of: transdermal administration, subcutaneous injection, intravenous injection, intraperitoneal injection, intramuscular injection, intrasternal injection, intrathecal injection and infusion techniques.

7. The method of claim 1, wherein the administration step comprises administering Congo Red or a pharmaceutically acceptable salt or derivative thereof along with a lipophilic solvent or carrier.

8. The method of claim 7, wherein said lipophilic solvent or carrier is selected from the group consisting of: DMZ, an organic solvent, phosphatidyl choline and cholesterol.

9. A method of treating a mammal having a condition associated with deposition of PrP-res related amyloidogenic protein in plaques, comprising:
   administering to said mammal a pharmacologically effective amount of Congo Red or a pharmaceutically acceptable salt or derivative thereof to interfere with PrP-res formation or to destabilize amyloidogenic protein structures already formed in said mammal.

10. The method of claim 9, wherein said condition is selected from the group consisting of: scrapie and transmissible spongioform encephalopathies (TSE's).

11. The method of claim 9, wherein the administering step comprises oral administration of Congo Red into said mammal.

12. The method of claim 9, wherein the administering step comprises parenteral administration of Congo Red into said mammal.

13. The method of claim 12, wherein the administering step comprises a technique selected from the group consisting of: transdermal administration, subcutaneous injection, intraperitoneal injection, intravenous injection, intramuscular injection, intrasternal injection, intrathecal injection and infusion techniques.

14. The method of claim 9, wherein the administration step comprises administering Congo Red along with a lipophilic solvent or carrier.

15. The method of claim 14, wherein said lipophilic solvent or carrier is selected from the group consisting of: DMZ, an organic solvent, phosphatidyl choline and cholesterol.

16. The method of claim 9, wherein said plaques occur in a tissue of the central nervous system of said mammal.

17. A method of treating a mammal having a condition associated with overproduction of PrP-res, comprising:
   administering to said mammal a pharmaceutically effective amount of Congo Red or a salt or derivative thereof in an amount sufficient to reduce the further production of PrP-res.

18. The method of claim 17, wherein said mammal is a human.

19. The method of claim 17, wherein said Congo Red is administered in a pharmacological composition comprising congo Red and a pharmaceutically acceptable carrier, filler or excipient.

20. The method of claim 17, wherein the administering step comprises oral administration of Congo Red into said mammal.

21. The method of claim 17, wherein the administering step comprises parenteral administration of Congo Red into said mammal.

22. The method of claim 21, wherein the administering step comprises a technique selected from the group consisting of: transdermal administration, subcutaneous injection, intravenous injection, intramuscular injection, intrasternal injection, intrathecal injection and infusion techniques.

23. The method of claim 17, wherein the administration step comprises administering Congo Red along with a lipophilic solvent or carrier.

24. The method of claim 23, wherein said lipophilic solvent or carrier is selected from the group consisting of: DMZ, an organic solvent, phosphatidyl choline and cholesterol.

25. A method of treating a mammal having a chronic infection associated with Acquired Amyloid protein, comprising:
   administering to said mammal a pharmaceutically effective amount of Congo Red or a salt or derivative thereof to interfere with amyloidogenic protein formation or to destabilize amyloidogenic protein structures already formed in said mammal.

26. The method of claim 25, wherein said chronic infection is selected from the group consisting of: tuberculosis, osteomyelitis, rheumatoid arthritis, granulomatous ileitis, and Mediterranean fever.

27. A method of treating a mammal having multiple myeloma associated with Idiopathic Amyloid protein, comprising:
administering to said mammal a pharmaceutically effective amount of Congo Red or a salt or derivative thereof to interfere with amyloidogenic protein formation or to destabilize amyloidogenic protein structures already formed in said mammal.

28. The method of claim 27, wherein said Idiopathic Amyloid is derived from the variable region portion of an immunoglobulin protein.

29. A method of treating a mammal having a condition associated with Alzheimer's Disease, comprising:
administering to said mammal a pharmacologically effective amount of Congo Red or a pharmaceutically acceptable salt or derivative thereof to interfere with amyloidogenic protein formation or to destabilize amyloidogenic protein structures already formed in said mammal.

30. The method of claim 29 wherein said mammal is a human.

31. The method of claim 29 wherein said amyloidogenic protein is Beta Protein.

32. The method of claim 29 wherein said administration comprises a technique selected from the group consisting of: transdermal administration, subcutaneous injection, intraperitoneal injection, intravenous injection, intramuscular injection, intrasternal injection, intrathecal injection and infusion techniques.

33. The method of claim 29 wherein said administration comprises administering Congo Red along with a lipophilic solvent or carrier.

34. The method of claim 33 wherein said lipophilic solvent or carrier is selected from the group consisting of: DMZ, an organic solvent, phosphatidyl choline and cholesterol.

* * * * *

UNITED STATES PATENT AND TRADEMARK OFFICE
CERTIFICATE OF CORRECTION

PATENT NO. : 5,276,059
DATED : January 4, 1994
INVENTOR(S) : Caughey et al

It is certified that error appears in the above-indentified patent and that said Letters Patent is hereby corrected as shown below:

Column 15, line 33, please delete "Creutzfeldt-Jakob of prp-res", and replace it with —associated with formation of Prp-res —.

Signed and Sealed this

Eighth Day of November, 1994

Attest:

BRUCE LEHMAN

*Attesting Officer*  *Commissioner of Patents and Trademarks*